United States Patent [19]

Carbon et al.

[11] Patent Number: 5,054,087
[45] Date of Patent: Oct. 1, 1991

[54] PROCESS AND APPARATUS FOR OPTICALLY CHECKING PERFORATIONS IN HOLLOW ARTICLES SUCH AS TURBINE BLADES

[75] Inventors: Vincent A. Carbon, Paris; Jean-Luc C. Meiffren, St. Germain Les Corbeil; Pierre M. Pailliotet, Morsang Sur Orge, all of France

[73] Assignee: Societe Nationale D'Etude Et De Construction De Moteurs D'Aviation "S.N.E.C.M.A.", Paris, France

[21] Appl. No.: 407,584

[22] Filed: Sep. 15, 1989

[30] Foreign Application Priority Data

Sep. 15, 1988 [FR] France .................. 88 12008

[51] Int. Cl.$^5$ ............................................. G01N 21/00
[52] U.S. Cl. ......................................... 382/1; 356/237
[58] Field of Search ................ 382/1; 380/8; 356/378, 356/237, 240; 364/507

[56] References Cited

U.S. PATENT DOCUMENTS

| | | | |
|---|---|---|---|
| 3,436,56 | 4/1969 | McCartney | 250/223 |
| 3,495,915 | 2/1970 | Watson et al. | 356/167 |
| 3,680,966 | 8/1972 | Cofek et al. | 356/241 |
| 4,484,081 | 11/1984 | Cornyn, Jr. et al. | 250/563 |
| 4,555,798 | 11/1985 | Broadbent, Jr. et al. | 382/8 |
| 4,687,328 | 8/1987 | Shiraishi et al. | 356/384 |
| 4,766,325 | 8/1988 | Merkenschlager et al. | 250/572 |
| 4,783,751 | 11/1988 | Ehrlich et al. | 364/506 |
| 4,803,639 | 2/1989 | Steele et al. | 364/507 |
| 4,901,361 | 2/1990 | Glenn et al. | 382/18 |

OTHER PUBLICATIONS

Microtecnic, No. 4, 1976, p. 30, Reader Service No. 39, Zurich, CH, "Rolls Royce Reduce Inspection Time From 3 Hours to 10 Minutes."

Primary Examiner—Leo H. Boudreau
Assistant Examiner—Steven P. Klocinski
Attorney, Agent, or Firm—Oblon, Spivak, McClelland, Maier & Neustadt

[57] ABSTRACT

A process for optically checking perforations in a hollow article, particularly the micro-perforations in the vicinity of the leading or trailing edge of a hollow turbine blade for a turbo-shaft engine, comprises illuminating the inner cavity of the article through an opening at one end thereof, scanning the length of the article by means of a video camera and making a record of the luminance of the reflected light received by the camera through the perforations to be checked, converting the sequence of the data thus collected into electric signals, storing the said signals in a computing and storage unit, and processing and comparing the signals with a predetermined train of reference signals derived from a standard article.

10 Claims, 9 Drawing Sheets

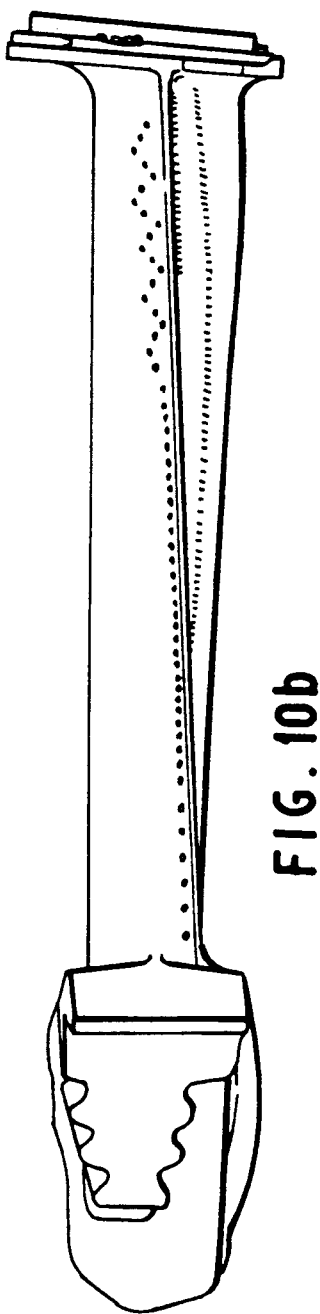
FIG. 10b
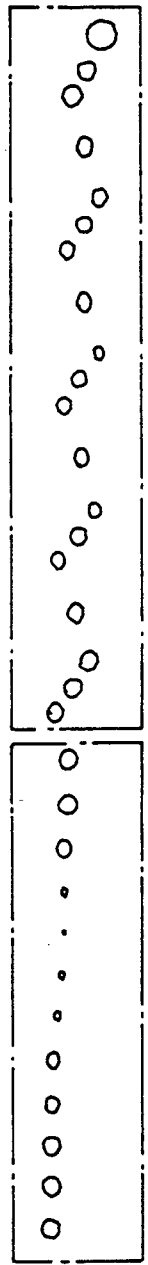
FIG. 12a
FIG. 12b
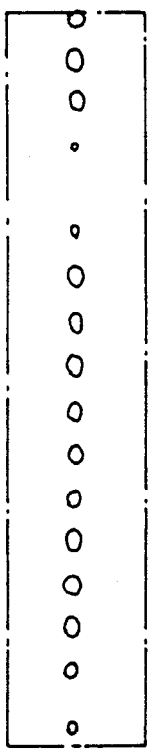
FIG. 12c

PROCESS AND APPARATUS FOR OPTICALLY CHECKING PERFORATIONS IN HOLLOW ARTICLES SUCH AS TURBINE BLADES

BACKGROUND OF THE INVENTION

1. Field of the Invention

The invention relates to a process and apparatus for optically checking perforations in hollow articles, and is particularly concerned with the checking of micro-perforations in aircraft engine parts such as combustion chamber walls, multi-perforated jackets of after-burner passages, and hollow turbine blades.

In such parts it is essential to be able to check, or even measure, the "permeability" of very small diameter holes. This permeability represents the capacity of the holes (perforations) to allow an aeration or cooling air flow through the wall in which they are drilled, and compliance with a minimum permeability is generally vital to the life of the part concerned.

Thus, in one example of cooled blades for the first turbine stage of a supersonic turbojet engine, in which the internal cavity of the blade is supplied with pressurized air through its root, each blade has one row of 53 perforations along its leading edge and two rows of 80 and 19 perforations along the trailing edge, all of the perforations having an average diameter of from 300 to 500 microns.

2. Summary of the prior art

The present method for checking the drilling quality of these holes consists of performing manually two operations. Firstly a gauge rod is inserted into each hole to check whether the hole is of a minimum diameter equal to that of the rod and whether the hole opens out into the internal cavity of the blade, and secondly the holes are counted to check that the intended number of holes have been provided.

In addition to the fact that this method is lengthy and tedious, the risks of error are great when counting the holes, and when checking the drilling by means of gauge rods, some holes may be omitted if the operator's attention is distracted. Moreover, these checks do not indicate whether the holes have been drilled in the right place, or whether the drilling accuracy (non-circular, etc.) is correct.

SUMMARY OF THE INVENTION

Accordingly, it is an object of the present invention to provide an optical method of checking the perforations of perforated hollow articles, particularly hollow turbine blades as described above, which method avoids all the above drawbacks and makes it possible to ensure rapid checking of the quality of the perforations, their number and the accuracy of their siting, with as little human intervention as possible.

A further object of the present invention is to provide practical apparatus for implementing the checking method which enables articles to be checked either individually or simultaneously.

According to the invention there is provided a process for optically checking the perforations of a hollow article having an internal cavity bounded by a wall provided with a plurality of perforations therethrough, and an opening into said cavity, comprising the steps of:

using a light source to illuminate the internal cavity of said article through said opening;

scanning a video camera along the outside of said article to receive light reflected from within said internal cavity outwardly through said perforations and thereby collect luminance data relating to said reflected light transmitted through said perforations;

converting the sequence of said collected luminance data into electrical signals;

storing said signals in a computing and storage unit; and processing said signals for comparison with a predetermined train of reference signals derived from a standard article.

The processing of the measurement signals may include a visual analysis of an image of the article on a video screen, with or without comparison on the screen with a reference article.

The processing may also include a step of analysing the intensity of the luminance of said light received by said camera, said analysis step being performed section by section of the video image provided by said camera.

Further according to the invention there is provided apparatus for carrying out a process for optically checking the perforations of a hollow article having an internal cavity bounded by a wall provided with a plurality of perforations therethrough, and an opening into said cavity, said apparatus comprising:

a source of coherent light;

means for focussing the light emitted from said coherent light source;

means for holding the article to be checked so that the focussed light from said light source enters said internal cavity of said article through said opening;

a video camera for receiving light reflected from within said cavity outwardly through said perforations;

a monitor screen connected to said video camera; and an image processing module connected to said video camera, said module comprising image storage units and units for processing digitized signals corresponding to each image produced by said camera.

In the case where it is desired to check a plurality of articles simultaneously using a single source of coherent light, such as a laser of p watts power, the apparatus comprises means for splitting the light beam emitted by said laser source into a plurality of beams of P/n watts power where n is the number of beams, focussing means for causing each of said plurality of beams to illuminate a respective one of said articles to be checked, and a separate video camera for each of said articles coupled to said image processing module, said module being adapted to record and process simultaneously the signals received from said video cameras.

Other characteristics of the checking process and apparatus in accordance with the invention will become apparent from the following description of the preferred embodiments with reference to the attached drawings.

BRIEF DESCRIPTION OF THE DRAWINGS

FIG. 10b is a photograph of the same blade showing the row of micro-perforations of the leading edge;

FIGS. 12a to 12c show similar images of the leading edge seen in FIG. 10b, FIG. 12a representing the part remote from the heel and FIG. 12c the part adjacent the heel;

DESCRIPTION OF THE PREFERRED EMBODIMENTS

Figure 1:
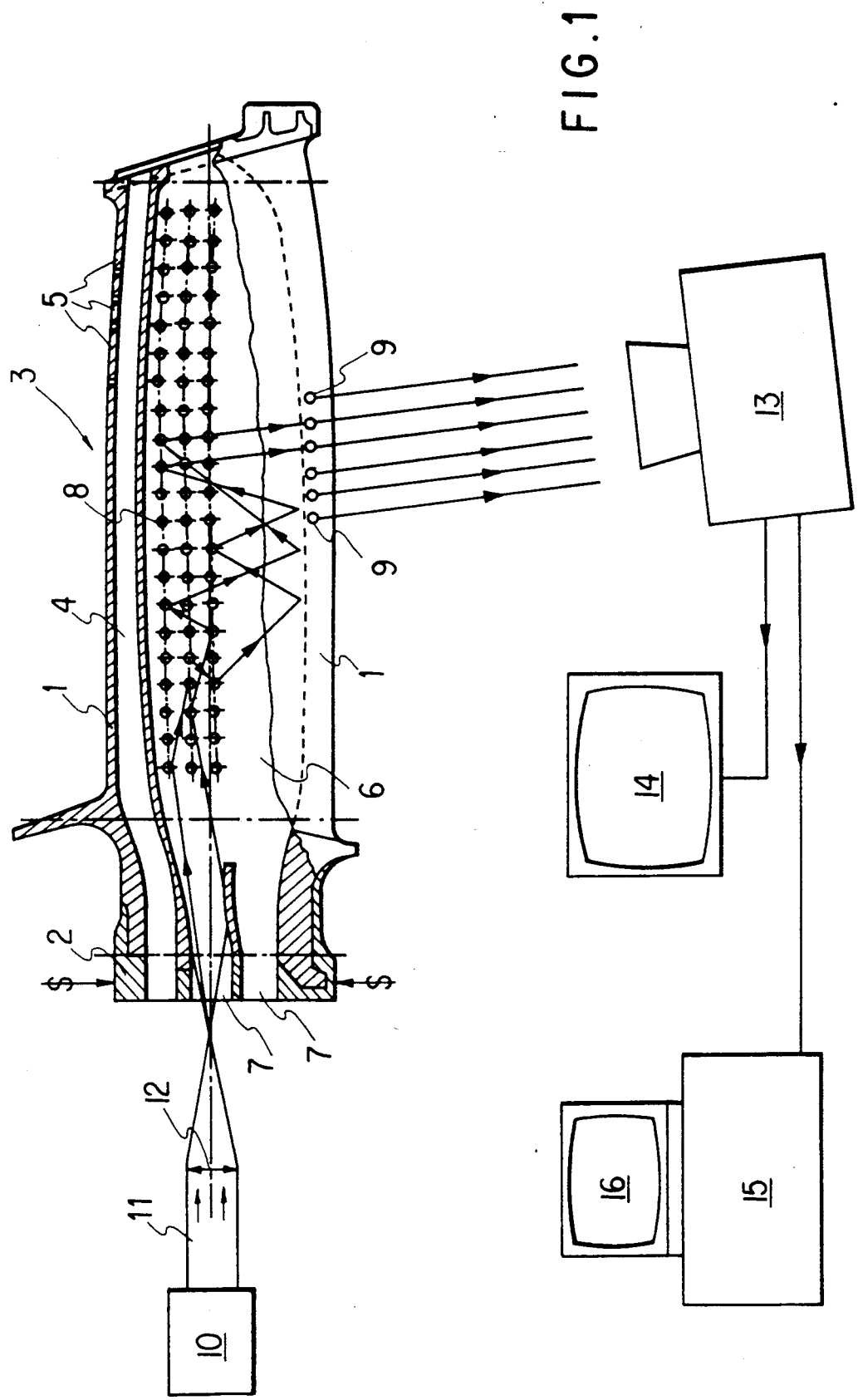
FIG. 1 is a schematic diagram showing the principle of the checking apparatus in accordance with the invention applied to the checking of a hollow turbine blade.

In FIG. 1 a section is shown of a hollow, air-cooled, model X blade 1 having a root 2 and a hollow aerofoil portion 3. In the example illustrated the blade has an upstream channel 4 in the vicinity of its leading edge which is supplied with cold air through the root 2, and the air is discharged through 53 micro-perforations 5 made in the extrados in the vicinity of the leading edge.

The blade also has a downstream cavity 6 supplied by two channels 7 in the blade root 2 and having internal turbulence points or studs 8. The air is discharged towards the trailing edge through two rows of micro-perforations 9 of about 500 microns in diameter, each row having respectively 80 and 19 perforations. The general principle of the invention resides in illuminating such a hollow blade from the inside, and examining and analyzing the radiated light which passes through the wall of the blade through the openings 5 or 9 in order to measure the number and characteristics of the openings.

To permit the implementation of this principle, the blade is illuminated by a source of coherent light, which in the present example is a continuously emitting laser tube 10 of the ionized argon type, of one watt power, which produces a light beam of 514.4 nanometers wavelength.

The light energy Es available at the outlet of the micro-perforations is equal to $Es = e^x Ee$, where x is the number of reflections of the radiation inside the cavity and Ee is the energy of the light emitted by the light source.

This energy Es is received by a video camera 13, and it is necessary that Es should be compatible with the energy levels detectable by such cameras, e.g. a few milliwatts for a CCTV type low luminance level camera. The image received by the camera 13 is transmitted to a video monitor 14 on which it can be interpreted by an operator.

The illuminating beam 11 is focussed by means of a convergent lens 12 and its optical axis is substantially oriented along the axis of symmetry of the cavity to be illuminated, in this case the downstream cavity 6. Depending on the internal structure of the blade being examined, the blade is positioned relative to the laser source 10 so as to promote a homogeneous distribution of light in the blade cavity. Furthermore, since the focussed light beam encounters on its travel a certain number of obstacles (i.e. the walls of the channels 7, studs 8, and the inner wall of the cavity 6), from which it is reflected, before issuing through the micro-perforations 5 or 9, it is important to limit the number of reflections of the rays of light in the cavity because at each reflection the intensity of reflected light Ir is equal to $Ir = e\, Ie$, where Ie is the intensity of incident light e is the overall efficiency linked with the reflectivity coefficient of the material.

For each reflection the following obtains:

$$e = \frac{(n_{air} - n_{metal})^2 + k^2}{(n_{air} + n_{metal})^2 + k^2}$$

with $n_{air}$ and $n_{metal}$ being indices of refraction in air and metal respectively and k being the absorption coefficient of the metal.

With respect to the materials used for making hollow blades the refraction indices "$n_{metal}$" of the said metals vary from 0.58 to 0.63 and the absorption coefficient is nil. Thus, for a model X blade made from a nickel-based alloy of the INCONEL 718 (trade name) type, comprising 19% Cr, 18% Fe, 5% Nb, and the remainder Ni, the efficiency e is equal to 0.057 for one reflection.

For another alloy used for model Y blades, which will be referred to later, i.e. a nickel-based alloy named DS 200 (trade name) comprising 12% W, 10% Co, 9% Cr, 5% Al, and the remainder Ni, the efficiency e is equal to 0.076.

The signals emitted by the camera 13 are also transmitted to an analogue/digital computer where they are digitized to be processed in an image processing module 15. By convolution processing and filtering, detection sensitivity is improved and the contrast between subsequent perforations and the remainder of the part is increased. In this way corrected images are recreated which it is possible to display on a screen 16 linked to the processing module 15. Moreover, as the image is stored, it is possible for each scanning to establish the luminance curve relating to the corresponding section of the part. The light intensity received point by point and digitized is a function of the diameter of the micro-perforation through which the corresponding ray of light issued. Thus, it is possible to make a finer analysis of the exact condition of the part.

Examples of operation will now be explained with reference to FIGS. 4 to 7.

Two types of hollow blades were examined by means of the apparatus in accordance with the invention. The two types of blades were high pressure turbine blades of a turboshaft engine, the first a model X blade made of INCONEL 718, and the second a model Y blade made of DS 200. The number of micro-perforations provided in the blades is summarised in the following table:

| PARTS | Micro-perforations existing | | Micro-perforations detected | | | |
|---|---|---|---|---|---|---|
| | | | Video image | | Corrected digitized image | |
| | leading edge | trailing edge | leading edge | trailing edge | leading edge | trailing edge |
| HP Blade Model X | 53 | 80 +19 | 53 | 80 +19 | | |
| HP Blade Model Y | 15 +15 int. +15 ext. | 14 | 14 +15 +15 | 14 | 15 15 15 | 14 |

Figure 4:
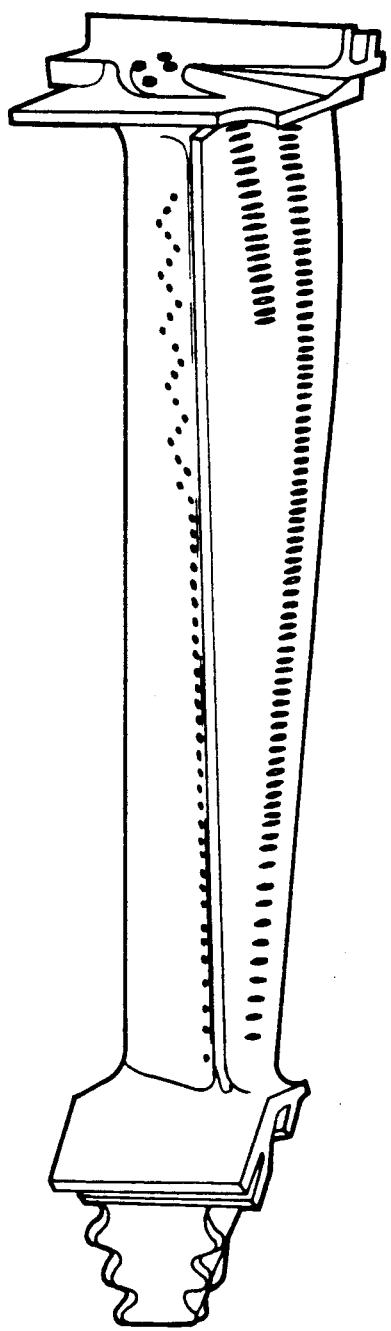
FIG. 4 shows a photograph of an example of a model X cooled turbine blade, the leading edge of which has one row of 53 holes, and the trailing edge of which has two rows of 80 and 19 holes for the outflow of air.

FIG. 4 is a photograph of the model X blade in which the trailing edge perforations may be seen.

Figure 5:
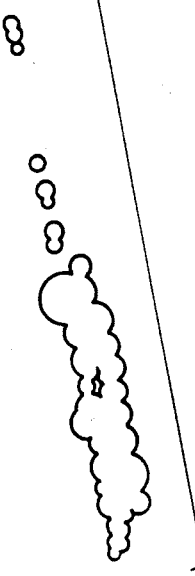
FIG. 5 shows a photograph of an optical image of the trailing edge of the blade shown in FIG. 4, obtained by means of a process in accordance with the invention.

FIG. 5 is a photograph of the optical signature of the trailing edge perforations such as may be seen on the video screen 14. It will be noted that all of the perforations are plotted on the photograph of FIG. 4. The two rows of perforations are visible and the number of perforations in each row can be counted.

Perforations appearing darker than the others must be interpreted as having a smaller diameter or as only partly clear.

Figure 6:
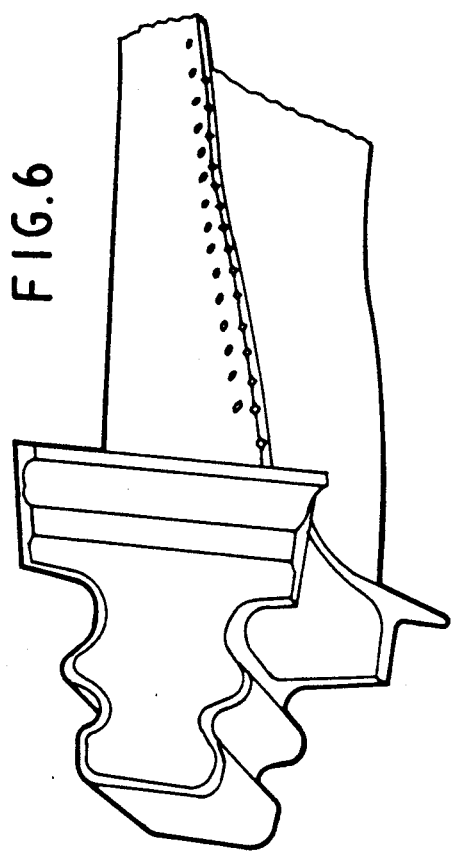
FIG. 6 shows a photograph of a model Y blade which has its leading edge provided with three rows of 15 air outflow holes.
Figure 7:
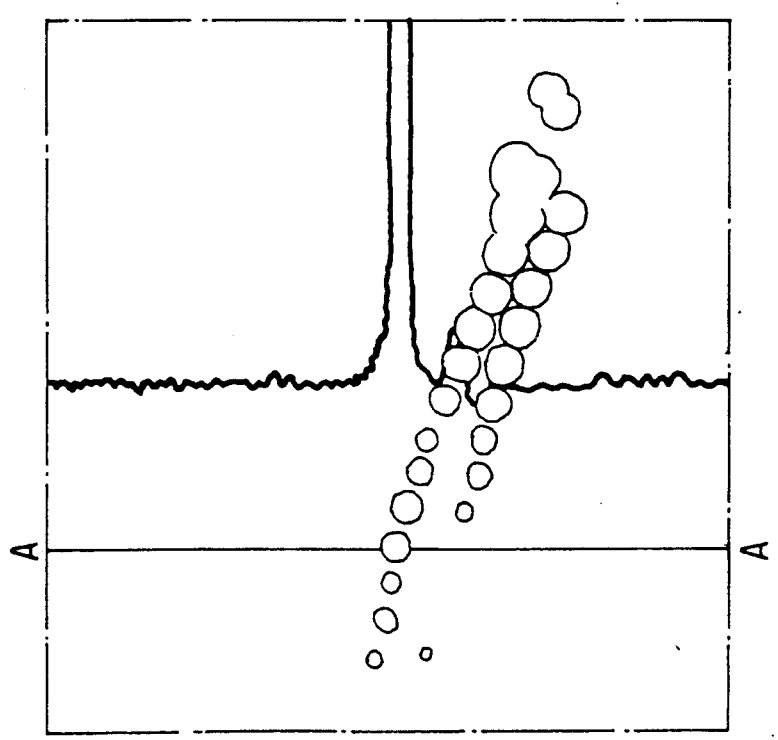
FIG. 7 shows a digitized image of the leading edge of the Y blade, viewed from the extrados side, and also the use of luminance curves for interpreting the results read on the digitized image.

FIG. 6 is a photograph of the leading edge of the model Y blade. In the photograph of FIG. 7 the digitally reconstituted processed image shows two of the three rows of 15 existing perforations. The orientation of the third row of perforations does not make it visible in the photograph.

Whereas the video image (similar to that of FIG. 5) enabled only 14 holes instead of the 15 existing holes to be counted in one of the two rows, the reconstituted image of FIG. 7 made it possible, through improvement of the contrast, to detect the 15 perforations expected.

The 15th hole, not visible in the video image, corresponds to section AA of FIG. 7.

Analysis of the luminance curve of the section AA of the part containing the majority of the perforations to be checked (chosen in a sectional plane substantially perpendicular to a direction along the article containing a majority of the perforations to be checked shows two peaks of intensity. The first peak 17a, of greater height, corresponds to an opening of normal diameter 18a, whereas the smaller second peak 17b discloses the existence of an opening 18b which the video image did not reveal. A more detailed analysis of the opening 18b showed that the latter opened out obliquely and that the diameter "visible" to the camera was 0.15 mm instead of the 0.50 mm of a normal opening. Such a defect in perforation geometry would not have been possible with the prior method of checking using gauge rods.

The digitizing processes and their results will now be discussed with reference to FIGS. 10 to 15d.

After digitization each peak of light intensity may be compared with a predetermined binarization threshold, which permits a qualitative and quantitative analysis in the counting of the open micro-perforations.

Figure 10A:
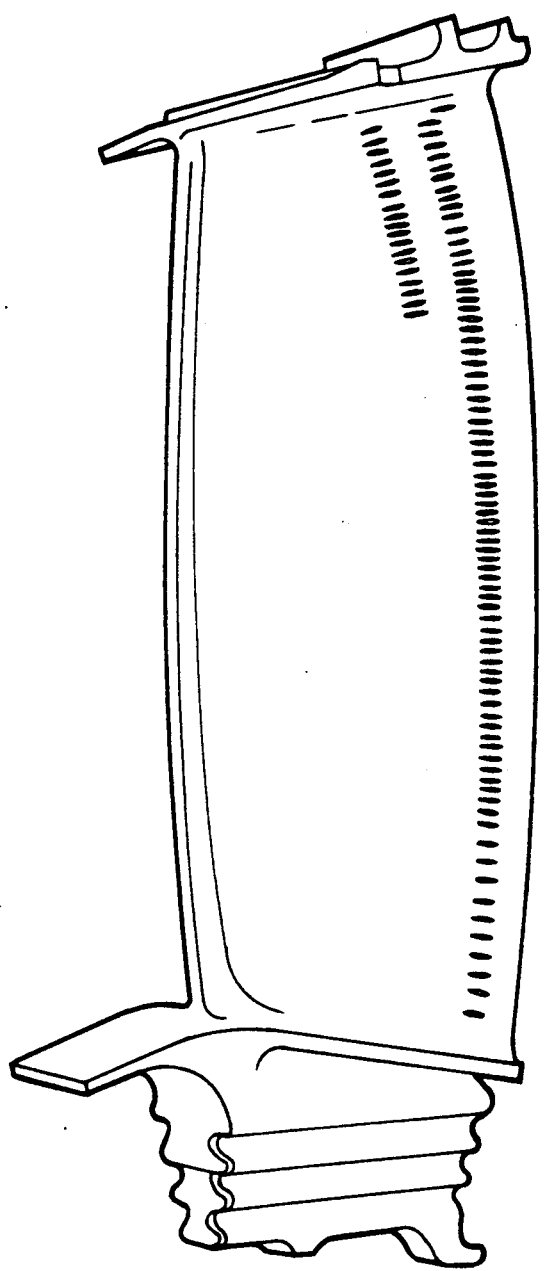
FIG. 10a is a photograph of the model X blade showing the micro-perforations of the trailing edge.
Figure 11A:
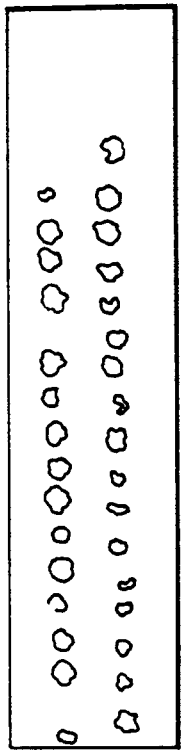
FIGS. 11a to 11d show images reconstituted by digitizing and thresholding the light signals derived from the openings of the trailing edge of the blade shown in FIG. 10a, with FIG. 11a representing the right-hand part of FIG. 10a and FIGS. 11b to 11d representing successive parts progressing left therefrom towards the blade root.
Figure 11B:
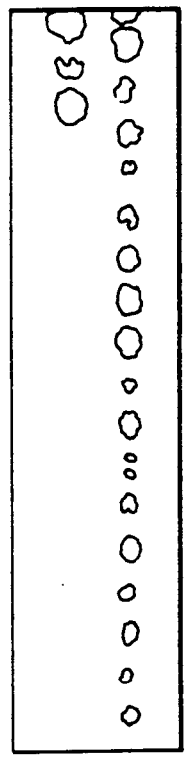
Figure 11C:
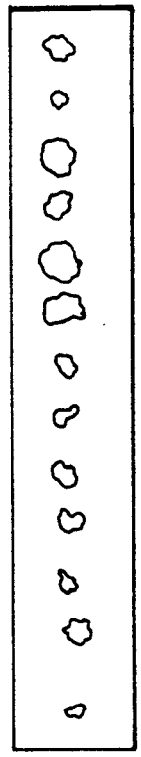
Figure 11D:
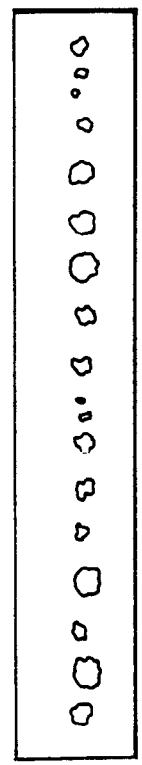

FIGS. 11a to 11d are the digitized images of the trailing edge photographed in FIG. 10a. In FIG. 11a it may be observed that between the fourth and fifth visible holes from the right of the top row, a dark gap longer than the others indicates a hole which does not open out, and in the bottom row the fifth hole from the right is observed to open out only slightly. This qualitative analysis may be quantified and the geometric parameters of the micro-perforations can be established.

Figure 15:
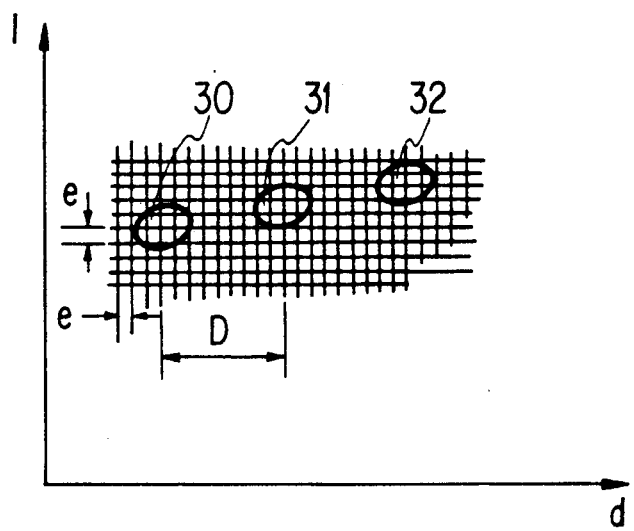
FIGS. 15 and 15a to 15d show various stages of a method for the fine calculation of skeleton images of the micro-perforations.

Thus, if reference is made to FIG. 15, a portion of the display screen of the image processing module 15 is shown, the screen being separated into pixels of size "e". Line scanning makes it possible to attribute to each pixel the binarized level of light intensity corresponding to a perforation or a non-perforated part of the surface. By counting the consecutive pixels illuminated it will be possible to ascertain the area of each micro-perforation and to determine the center of intensity of each micro-perforation, which is equated to the geometric center of the perforation.

Having established the center of each micro-perforation it is possible to deduce therefrom the distance separating consecutive center and thus the distance between the holes.

It is also possible from this measurement to calculate the line of least squares for each generatrix of micro-perforations and to determine the dispersion of each perforation relative to this line of least squares.

A second method of processing permits refinement of the parameters just discussed.

For each micro-perforation it is possible to calculate, pixel by pixel, the mean value of the grey level of each pixel of a perforation, i.e. the value $I_d$ of the intensity at the level of the pixel at abscissa d related to the area $e^2$ of said pixel, which makes it possible to achieve an enhanced contrast of the image of each perforation.

Using this method, it is possible to optimize the measurement of the radius of each perforation and to eliminate from the digitized image aberrant points introduced into the measurement chain either by the optical system or by the image system, this being achieved by eliminating from the reconstituted image the points whose processed radius computed on the mean value of grey levels would be lower than an imposed minimum value.

Similarly, using said "mean values of grey levels", it is possible to recompute all the preceding data (distance between perforations, dispersion of holes, their areas) in a finer manner.

If it is desired to make a quantitative analysis on an overall image of a row of perforations, it will be possible to carry out an extraction of outline for each perforation, i.e. to form a "skeleton image".

Figure 13:
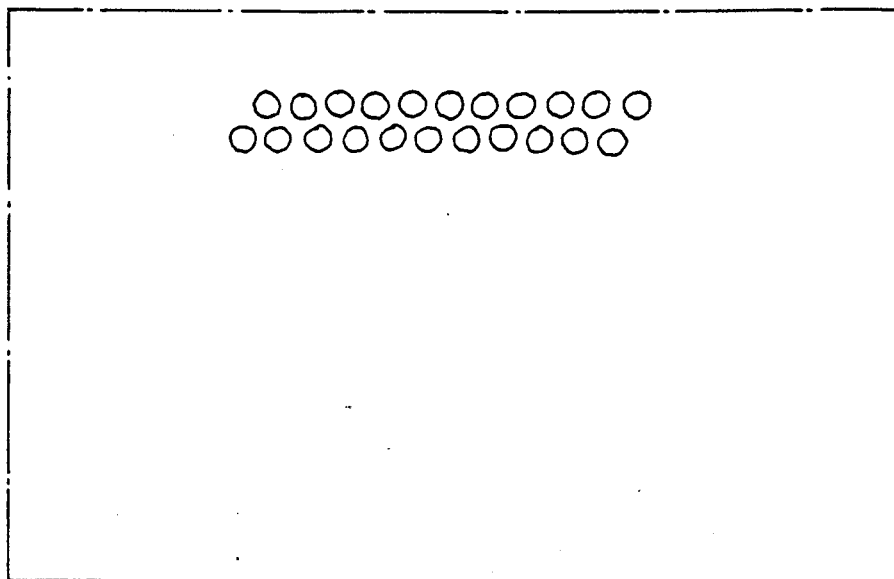
FIG. 13 is a reconstructed image of the trailing edge of a model Z blade having two rows of 11 micro-perforations.

FIG. 13 shows the binarized image of a double row of perforations at the trailing edge of a model Z blade, such as obtained by the processes described above, whereas FIG. 14 shows the same as a "skeleton image" obtained as follows.

Figure 8:
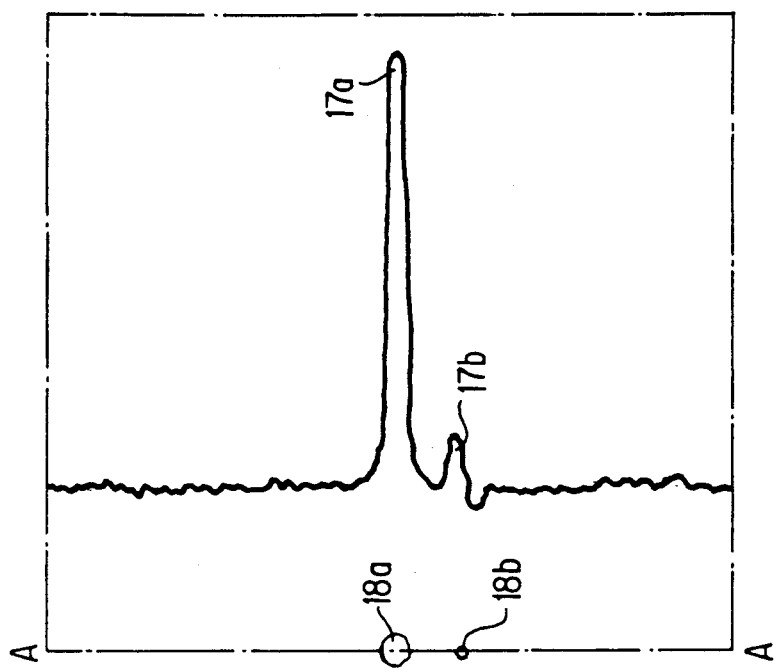
FIG. 8 shows the luminance curve corresponding to the section AA in FIG. 7.
Figure 9:
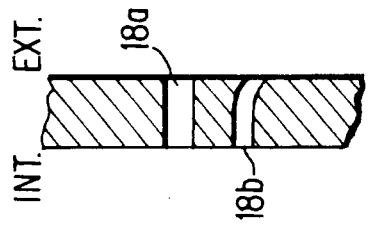
FIG. 9 shows the perforation fault in the section AA of the blade in the photograph of FIG. 7, as revealed by analysis.

As observed in FIGS. 7 and 8 the light intensity curve for each scanning is disturbed by a noise factor. The same applies to the grey levels calculated earlier. The aim of the outline extraction method is to determine with extreme precision the edge of each micro-perforation.

Figure 15A:
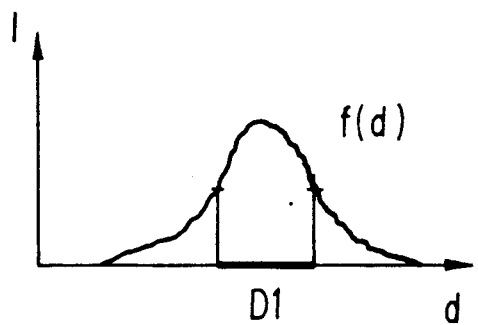
Figure 15B:
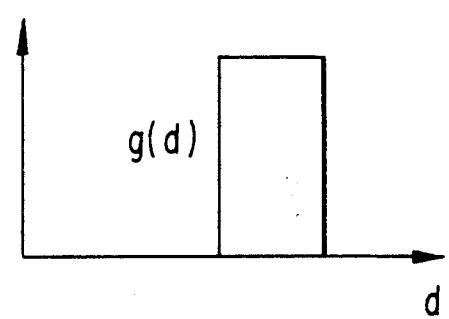
Figure 15C:
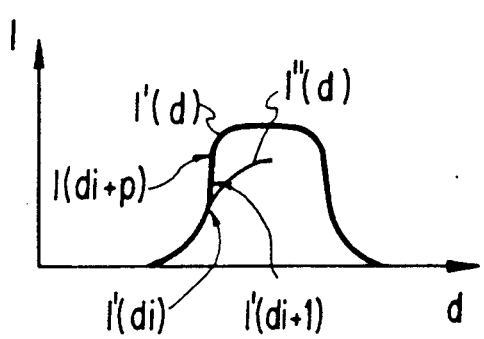
Figure 15D:
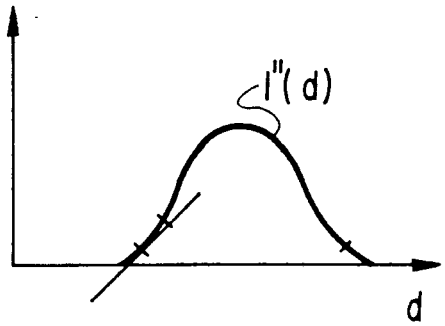

To do this, at each scanning and for each perforation determining a grey level peak, the grey level intensity curve I=f(d) is determined (FIG. 15a). To this function is added an interval function g=g(d) (FIG. 15b), and a smoothing is made at p points of the obtained curve I'=f(d)+g(d), the smoothed value $$\frac{I'(d_i) + I'(d_{i+1}) + \ldots + I'(d_{i+p})}{p}$$

being reallotted to the mean index point to provide a curve I''(d) which is eroded (suppressing the ill-timed noise peaks), expanded (by the addition of the function g(d)), and smoothed. From this curve the value α of the tangent coefficient corresponding to the inflection point of the smoothed curved I''(d) is extracted.

This operation is performed at each scanning and for each perforation, the values thus established and stored permitting a reconstruction of the precise outline of each perforation.

Figure 14:
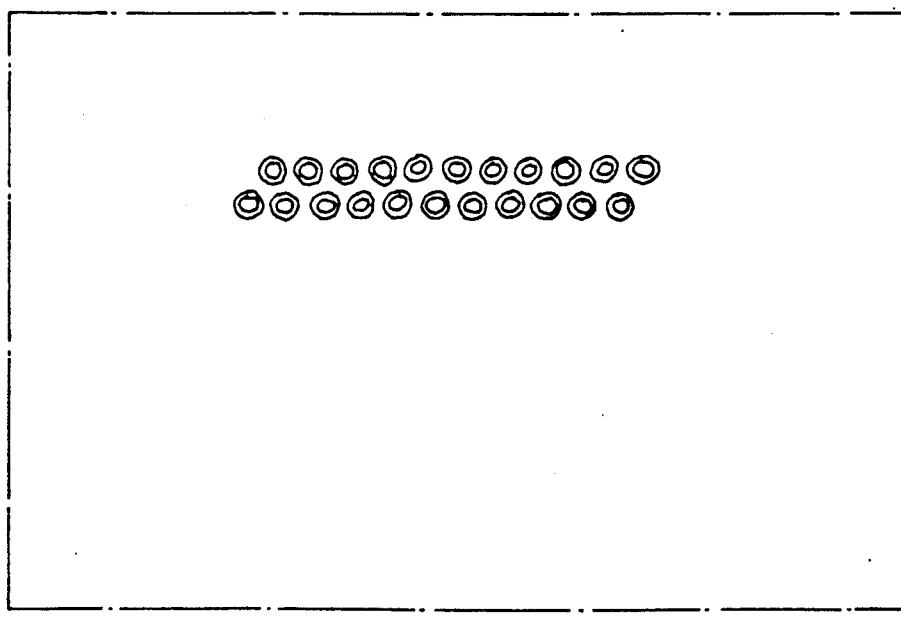
FIG. 14 is a photograph of the image of FIG. 13 processed to extract the outline of each micro-perforation.

The photograph of FIG. 14 shows the reconstruction of the outline of each perforation of FIG. 13 by this method, each point of each outline having been determined by the method indicated above.

All parameters (area of perforations, spaces between perforations, dispersion) can thus be recalculated with extreme precision.

Figure 2:
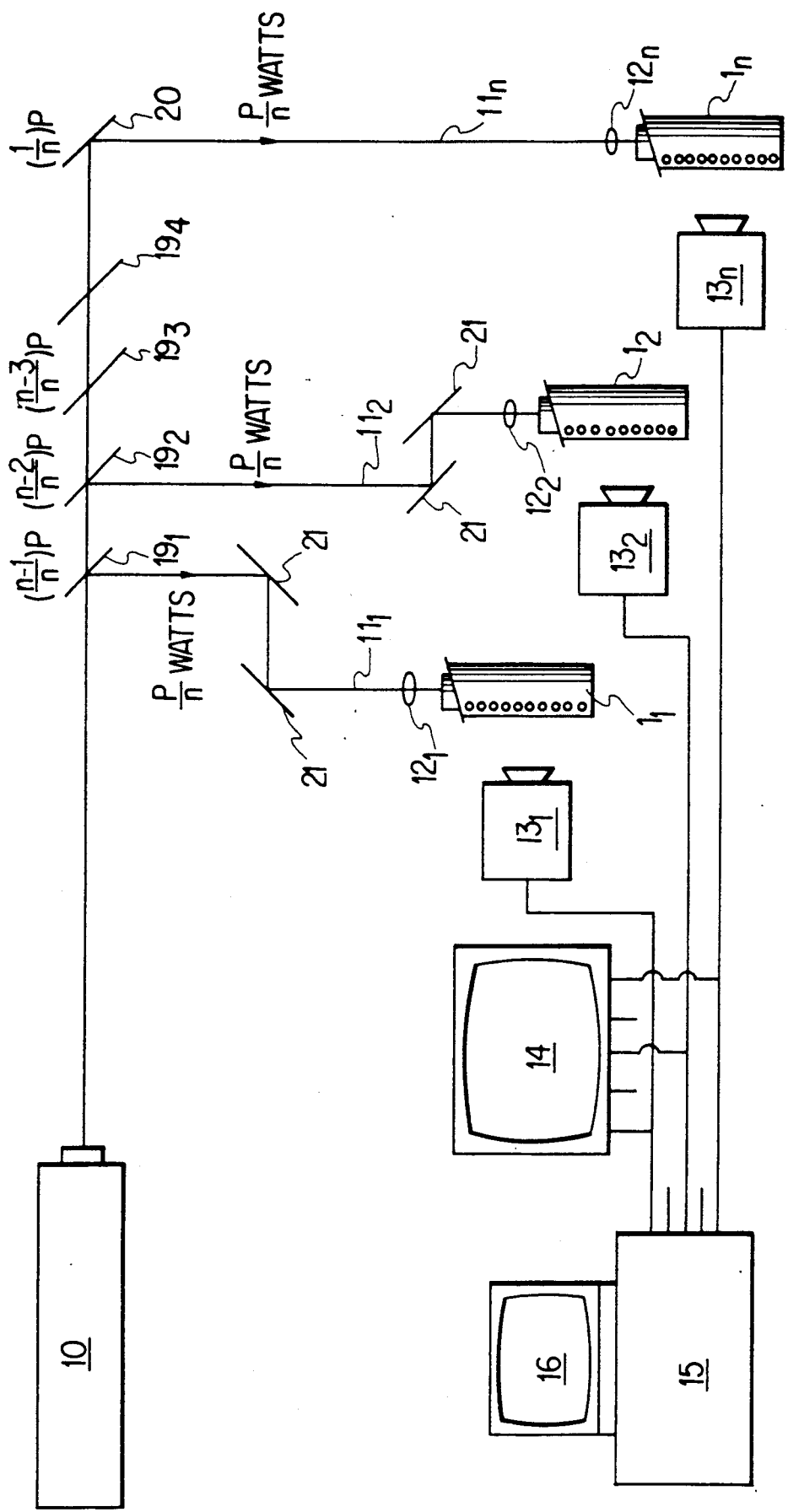
FIG. 2 is a schematic diagram of an embodiment of the apparatus for the simultaneous checking of several blades.

The method of checking in accordance with the invention has just been described in relation to the checking of a single article. However, the method may be extended to the simultaneous checking of several articles. For example, as shown in FIG. 2, (n−1) plate or prism beam splitters $19_i$ in series with a mirror 20 may be interposed between the laser 10 and the n articles to be checked. The first splitter $19_1$ reflects a ray of P/n power and transmits to the second splitter $19_2$ a power of (n−1)/n P watts. The same applies to the second splitter $19_2$ which transmits (n−2)/n P watts and so on up to the mirror 20 which receives and reflects the last fraction P/n of the power from the source 10.

By means of mirrors 21 each split laser beam $11_i$ is directed to the respective article $1_i$ to be checked, before which it is focussed by a lens $12_i$.

For each article the reflection principle of operation is identical with that described earlier, the apparatus comprising n cameras $13_i$ in parallel, and the image processing module 15 having n parallel stores and one processing unit permitting the reconstruction of n corrected images of the articles checked.

Figure 3:
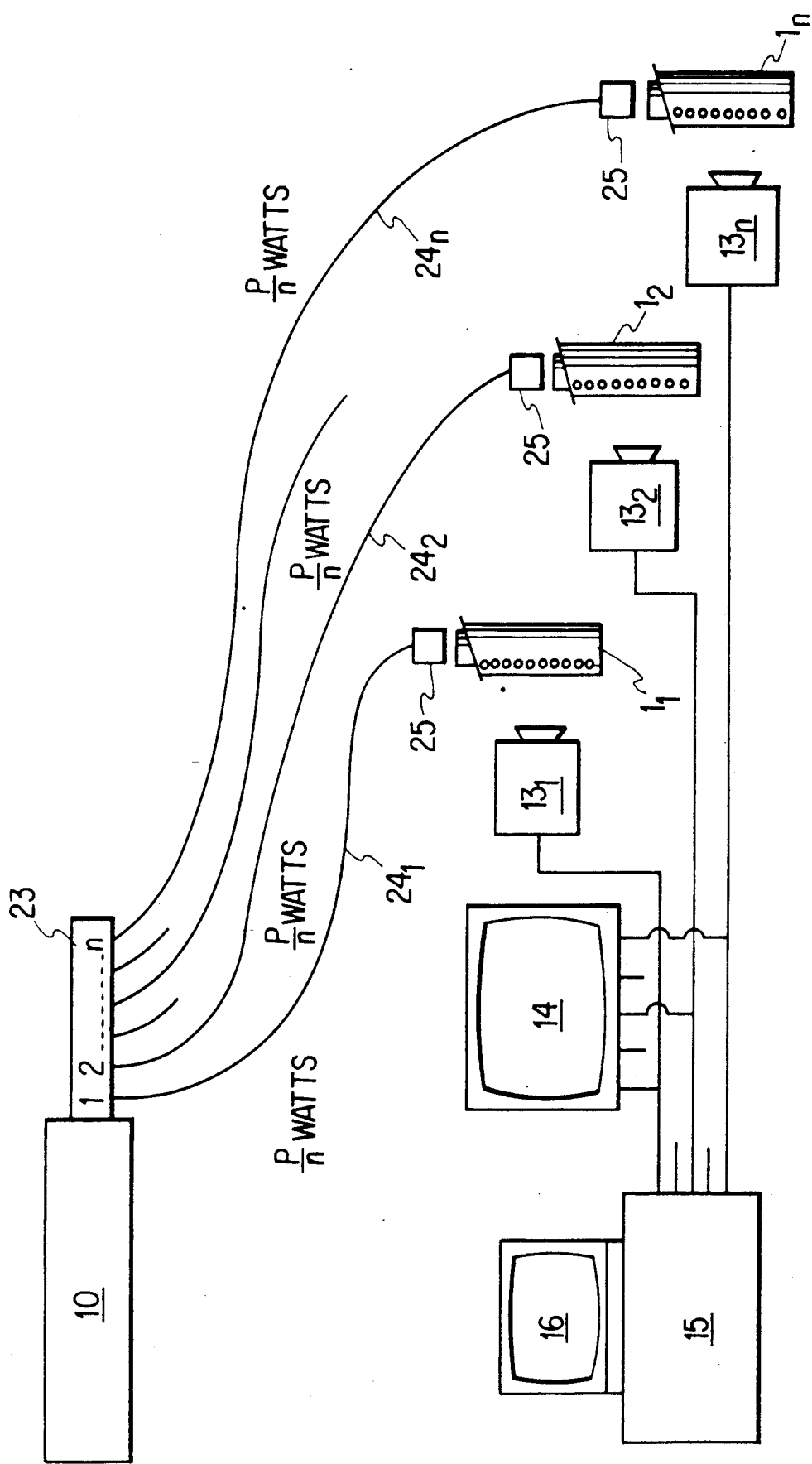
FIG. 3 is a schematic diagram of an alternative embodiment for simultaneously checking a plurality of blades.

In an alternative arrangement shown in FIG. 3, the detection and computing means are identical with those of the system of FIG. 2. The essential difference lies in the laser beam transmission means used, the laser 10 of P watts power emitting radiation into an optical splitter assembly 23 having n outputs constituted by optical fibres $23_i$ each arranged at its end with means 25 for focussing the beam on the article $1_i$ to be checked.

The apparatus in accordance with the invention may also be automated to improve the checking rate by the addition of a gripping device for the articles and a robot which positions the articles before each checking and turns those parts whose leading edge and trailing edge perforations have to be checked. Alternatively each article may remain stationary and a robot used to carry the image collecting camera.

In addition, by permitting a comparison of the values of a checked article with the reference values of a standard article stored in the computing unit, it is possible to give a check verdict for each article pointing out the conformity of the number of perforations, their diameter and the distance between them.

Thus, the proposed method considerably improves checking quality and speed, and it also permits checking perforations whose diameter may have decreased down to 10 microns. Below this value a light beam parallel with the inlet to the perforation to be checked would be diffracted as it passes through, thus making the method impracticable.

We claim:

1. A process for optically checking the perforations of a hollow article having an internal cavity bounded by a wall provided with a plurality of perforations therethrough, and an opening into said cavity, comprising the steps of:
   using a light source to illuminate the internal cavity of said article through said opening;
   scanning a video camera along the outside of said article to receive light reflected from within said internal cavity outwardly through said perforations and thereby collect luminance data relating to said reflected light transmitted through said perforations;
   converting the sequence of said collected luminance data into electrical signals;
   storing said signals in a computing and storage unit; and
   processing said signals for comparison with a predetermined train of reference signals derived from a standard article;
   wherein said processing of the signals includes the steps of
   binarizing said signals, the area seen by said camera being divided into pixels of known dimensions;
   effecting section by section processing of the grey level intensity curve I=f(d) where d is the coordinate along the section axis;
   performing an erosion-expansion treatment by the addition of an interval function g(d) where g assumes the values 0 or 1 depending on the length d;
   affecting smoothing on a plurality of p points of the curve I'=f(d)+g(d) thus obtained, the smoothed value $$\frac{I'(d_i) + I'(d_{i+1}) + \ldots I'(d_{i+p})}{p}$$

being reallotted to the mean index point between i and i+p to obtain a smoothed intensity curve I''(d);
   extracting the point of inflection of the curve I''(d); and
   reconstructing the skeleton image of each open-perforation.

2. A process according to claim 1, including the step of displaying an optical signature of said article scanned by said video camera on a video screen for visual analysis of said optical signature.

3. A process according to claim 1, wherein said article is arranged in such a manner that the axis of symmetry of said internal cavity is in the vicinity of the optical axis of said light source which illuminates said cavity.

4. A process according to claim 1, wherein said article and said light source are arranged so that the number of intermediate reflections experienced by said light emitted by said light source into said internal cavity of said article before said light passes out through said perforations is restricted to a value x such that the output light energy Es transmitted through said perforations is compatible with the light energy detectable by said video camera, said output light energy Es being linked to the energy Ee of the light emitted by said light source by the relation $Es = e^x Ee$, where e is the overall efficiency of transmission as a function of the total number of reflections and of the reflectivity coefficient of the material of the article, and x is the said number of intermediate reflections.

5. A process according to claim 1, wherein said article is a hollow blade for a turbine of a turbomachine, and said perforations are micro-perforations in the vicinity of the leading or trailing edge of said blade, said opening into said internal cavity of said blade being located in the root of said blade.

6. Apparatus for carrying out a process for optically checking the perforations of a hollow article having an internal cavity bounded by a wall provided with a plurality of perforations therethrough, and an opening into said cavity, said apparatus comprising:
   a source of coherent light;
   means for focussing the light emitted from said coherent light source;
   means for holding the article to be checked so that the focussed light from said light source enters said internal cavity of said article through said opening;
   a video camera for receiving light reflected from within said cavity outwardly through said perforations;
   a monitor screen connected to said video camera; and
   an image processing module connected to said video camera,
   said module comprising image storage units and units for processing digitized signals corresponding to each image produced by said camera,
   wherein said image processing module includes computing means for analysing an luminance intensity curve of the light emitted by said perforations sections by section of the displayed image of said perforations.

7. Apparatus according to claim 6, wherein said image processing module includes computing means for processing said signals, by convolution and filtering, to provide corrected images of a light signature of said perforations.

8. Apparatus according to claim 6, for simultaneously checking a plurality of said articles, wherein said source of light is a laser of p watts power, and said apparatus comprises means for splitting the light beam emitted by said laser source into a plurality of beams of P/n watts power where n is the number of beams, focussing means for causing each of said plurality of beams to illuminate a respective one of said articles to be checked, and a separate video camera for each of said articles coupled to said image processing module, said module being adapted to record and process simultaneously the signals received from said video cameras.

9. Apparatus according to claim 8, wherein said beam splitting means comprises a plurality of beam splitters of the plate or prism type arranged in series.

10. Apparatus according to claim 8, wherein said beam splitting means comprises a splitter box having a plurality of outputs constituted by optical fibres, each fibre being adapted to convey a beam of P/n watts power and having integrated optical focussing means at its end remote from said splitter box.

* * * * *